United States Patent [19]

Shibasaki et al.

[11] Patent Number: 4,728,746
[45] Date of Patent: Mar. 1, 1988

[54] β-AMINOTHIOL ESTER AND PROCESS FOR PREPARING THEREOF

[75] Inventors: Masakatsu Shibasaki, Mitaka; Takamasa Iimori, Sagamihara, both of Japan

[73] Assignee: Sagami Chemical Research Center, Tokyo, Japan

[21] Appl. No.: 794,893

[22] Filed: Nov. 4, 1985

[30] Foreign Application Priority Data

Nov. 5, 1984 [JP] Japan .................................. 59-231151
Nov. 5, 1984 [JP] Japan .................................. 59-231152

[51] Int. Cl.⁴ .................. C07C 153/09; C07D 315/00; C07F 7/02; C07F 7/04
[52] U.S. Cl. .................................. 558/252; 549/419; 556/410; 556/418
[58] Field of Search .................. 558/252; 549/419; 556/410, 418

[56] References Cited

PUBLICATIONS

Inomata et al., (Bull. Chem. Soc. Jap.), CA 79: 66428h.
Tetrahedron Letters, vol. 24, No. 2, pp. 217–220 (1983).
Tetrahedron Letters, vol. 23, No. 22, pp. 2293–2296 (1982).
Tetrahedron Letters, vol. 22, pp. 913–916 (1981).
Tetrahedron Letters, vol. 21, pp. 2783–2786 (1980).
Tetrahedron Letters, vol. 22, No. 51, pp. 5205–5208 (1981).
Emori et al, Tetrahedron Letters, vol. 26, No. 12, 1985, pp. 1523–1526.
Chemical Abstracts, vol. 89, No. 13, Sep. 25, 1978, p. 297, col. 2, Abstract No. 102305h.
Chemical Abstracts, vol. 87, No. 23, Dec. 5, 1977, p. 651, col. 1, Abstract No. 184931e.

Primary Examiner—Henry R. Jiles
Assistant Examiner—Robert C. Whittenbaugh
Attorney, Agent, or Firm—Armstrong, Nikaido, Marmelstein & Kubovcik

[57] ABSTRACT

β-Aminothiol ester having the general formula (I):

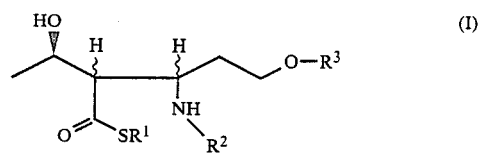

which is useful as an intermediate in the preparation of carbapenen beta-lactam antiobiotics, wherein $R^1$ is alkyl or aryl and $R^2$ and $R^3$ are protective groups. The β-Aminothiol ester of formula (I) is prepared by reacting a β-hydroxythiol ester having the general formula (III):

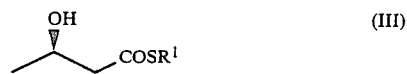

wherein $R^1$ is as above, with a boron compound having the general formula (IV):

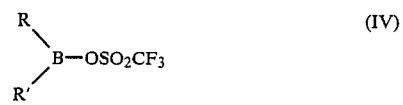

wherein each of R and R' is alkyl or cycloalkyl, or R and R' taken together, form a ring including the boron atom in the presence of a tertiary amine, the obtained reaction mixture being reacted with an imine having the general formula (V):

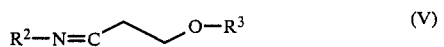

Wherein $R^2$ and $R^3$ are protective groups, followed by treating the resultant product with hydrogen peroxide.

3 Claims, No Drawings

β-AMINOTHIOL ESTER AND PROCESS FOR PREPARING THEREOF

BACKGROUND OF THE INVENTION

The present invention relates to β-aminothiol ester having the general formula (I):

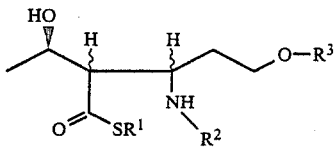

wherein $R^1$ is alkyl group or aryl group and $R^2$ and $R^3$ are protective groups, and a process for preparing thereof.

β-Aminothiol ester of the present invention having the general formula (I) can be converted to carbapenem β-lactam antibiotics such as thienamycin. Carbapenem β-lactam antibiotics are such compounds that are greatly expected as β-lactam antibiotics of the fourth generation since they show an excellent antimicrobial activity to almost all species of bacteria including Pseudomonas aeruginosa with intensity exceeding that of the prior drugs and have an excellent stability against β-lactamase.

Carbapenem β-lactam antibiotics are produced by fermentation with only a low productivity and thus, industrially, they cannot but be prepared by a chemical synthesis, which is a point quite different from conventional penicillin antibiotics or cephalosporin antibiotics.

It is known by the person skilled in the art that basic intermediates for synthesis of carbapenem β-lactam antibiotics, some of which have already been applied to clinical usage, are β-lactam compounds having the general formula (II):

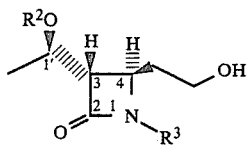

wherein $R^2$ and $R^3$ are protective groups.

β-Aminothiol ester of the present invention having the general formula (I) is a useful intermediate for synthesis of the β-lactam compound having the general formula (II) to be converted to an optically active β-lactam with a small number of steps by forming a β-lactam ring, protecting the hydroxy group and deprotecting the protective group (cf. Reference Examples).

Hitherto, the β-lactam compound having the general formula (II) has been prepared by the following process:

(1) A process which comprises forming a monocyclic β-lactam ring having a side chain at the 4-position by using an optically active amino acid or an asymmetric synthesis with enzyme, followed by introducing a side chain at the 3-position, (2) A process which comprises selectively forming the compound with asymmetric carbon atoms at the 3-position, 4-position and 1'-position by a particular means to be cyclized to β-lactam ring, and (3) A process which comprises forming a monocyclic β-lactam ring having a side chain at the 3-position by using L-threonine or an optically active penicillin, followed by introducing a side chain at the 4-position (cf. Masayuki Shibuya, Yukigoseikagaku Kyokaishi, 41, 62 (1983)).

However, the above process (1) is not suitable for industrial production since the introduction of a side chain at the 3-position is relatively hard, which makes the process unsuitable for synthesis on a large scale. Though the process (2) is employed in industry, it has defects such as a large number of production steps and involving an optical resolution. The process (3) also has a defect of a large number of production steps, though it gives a desired compound in an optically active form.

SUMMARY OF THE INVENTION

According to the present invention, there are provided β-aminothiol ester having the general formula (I), which makes it possible to synthesize β-lactam compound having the general formula (II) in an easy way and with a small number of steps, and a process for preparing thereof.

DETAILED DESCRIPTION

β-Aminothiol ester of the present invention having the general formula (I) is prepared by reacting β-hydroxythiol ester having the general formula (III):

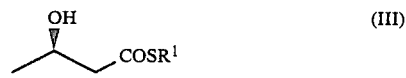

wherein $R^1$ is alkyl group or aryl group, with boron compound having the general formula (IV):

wherein R and R' are alkyl group or cycloalkyl group or, taken together, they can form a ring including boron atom in the presence of tertiary amine, the obtained reaction mixture being reacted with imine having the general formula (V):

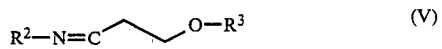

wherein $R^2$ and $R^3$ are protective groups, followed by treating the resultant with hydrogen peroxide.

β-Hydroxythiol ester having the general formula (III) is prepared in accordance with the following reaction scheme:

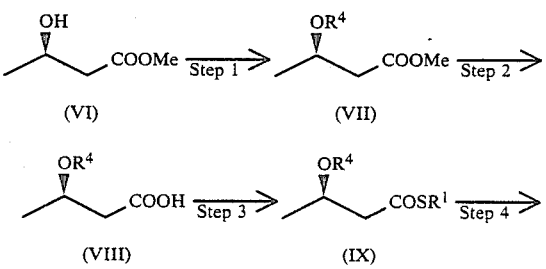

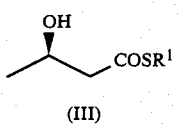

(III)

wherein $R^1$ is alkyl group or aryl group and $R^4$ is a protective group for hydroxyl group.

[STEP 1]

In the process of Step 1, the hydroxyl group of a β-hydroxy ester having the general formula (VI) is protected to form β-alkoxy ester having the general formula (VII). The starting β-hydroxy ester having the general formula (VI) can be prepared by oxidation of butanoic acid employing microorganisms on an industrial scale at an extremely low cost.

For the protection of hydroxyl group, t-butyldimethylsilyl ether, tetrahydropyranyl ether, and the like are employed. In case of t-butyldimethylsilyl ether, the protection proceeds easily in dimethylformamide (DMF) in the presence of t-butyldimethylsilyl chloride-imidazole. In case of tetrahydropyranyl ether, the protection is carried out in methylene chloride in the presence of dihydropyran-p-toluenesulfonic acid.

The reaction proceeds easily at 0° C. to room temperature.

[STEP 2]

In the process of Step 2, the β-alkoxy ester having the general formula (VII) obtained by the process of Step 1 is hydrolyzed to produce the β-alkoxy carboxylic acid having the general formula (VIII). The hydrolysis is carried out by employing bases such as potassium hydroxide and sodium hydroxide in alcoholic solvent containing water such as methanol containing water or ethanol containing water.

The reaction proceeds easily at 0° C. to room temperature.

[STEP 3]

In the process of Step 3, the β-alkoxy carboxylic acid having the general formula (VIII) obtained by the process of Step 2 is subjected to dehydration condensation reaction with aryl mercaptan or alkyl mercaptan to form a β-alkoxythiol ester having the general formula (IX). The dehydration condensation reaction is carried out in the presence of a catalytic amount of 4-dimethylaminopyridine and dehydrating agent such as dicyclohexylcarbodiimide (DCC). Examples of thiol compound employed are, for instance, benzenethiol, t-butyl mercaptan, ethanethiol, sec-butyl mercaptan, n-propyl mercaptan, isopropyl mercaptan, and the like. The reaction is conducted in a solvent which is a halogenated hydrocarbon such as methylene chloride or chloroform and proceeds easily at 0° C. to room temperature.

[STEP 4]

In the process of Step 4, the β-alkoxythiol ester having the general formula (IX) obtained by the process of Step 3 is deprotected to produce β-hydroxythiol ester having the general formula (III).

The deprotection can be carried out in a medium of acetic acid—water—tetrahydrofuran in both cases of t-butyldimethylsilyl ether and tetrahydropyranyl ether as a protective group for hydroxyl group.

The reaction proceeds easily at room temperature to 70° C.

Examples of the β-hydroxythiol ester having the formula (III) are, for instance, S-phenyl-3(R)-hydroxybutanethioate, S-t-butyl-3(R)-hydroxybutanethioate, S-ethyl-3(R)-hydroxybutanethioate, S-sec-butyl-3(R)-hydroxybutanethioate, S-n-propyl-3(R)-hydroxybutanethioate, S-isopropyl-3(R)-hydroxybutanethioate, and the like.

The boron compound having the general formula (IV) is easily obtained in the industrial manner. Examples of such compound are, for instance, 9-borabicyclo[3.3.1]nonyl trifluoromethanesulfonate, dicyclopentyltrifluoromethanesulfonyloxyborane, di-n-butyltrifluoromethanesulfonyloxyborane, and the like.

The reaction between the β-hydroxythiol ester having the formula (III) and the boron compound having the general formula (IV) must be carried out in the presence of a tertiary amine such as diisopropylethylamine, triethylamine, trimethylamine or tributylamine, diisopropylethylamine being preferable for efficiency of the reaction.

The reaction is conducted in a solvent, for example, halogenated hydrocarbon such as methylene chloride, chloroform or 1,2-dichloroethylene, ether such as diethyl ether, tetrahydrofuran (THF), dimethoxyethane (DME), or aromatic hydrocarbon such as toluene or xylene. The reaction proceeds smoothly, usually at −78° C. to room temperature.

The reaction mixture obtained in the reaction is reacted with an imine having the general formula (V). Examples of such imine having the general formula (V) are, for instance, N-3-benzyloxypropylidenebenzylamine, N-3-benzyloxypropylidene-p-methoxyanisidine, N-3-benzyloxypropylidene-o-methoxyanisidine, N-3-benzyloxypropylidenetrimethylsilylamine, N-3-benzyloxypropylidenetriethylsilylamine, N-3-benzyloxypropylidene-t-butyldimethylsilylamine, N-3-tetrahydropyranyloxypropylidenebenzylamine, N-3-t-butyldimethylsilyloxypropylidenebenzylamine, N-3-triethylsilyloxypropylidenebenzylamine, N-3-t-butyldimethylsilyloxypropylidenetrimethylsilylamine, and the like.

The reaction is carried out in the same solvent as that used in the reaction between the β-hydroxythiol ester and boron compound and proceeds easily at −78° C. to room temperature.

After the reaction with imine, the resultant is treated with hydrogen peroxide to give the β-aminothiol ester having the general formula (I) of the present invention. THe hydrogen peroxide employed is usually an aqueous solution of around 30%. The amount of hydrogen peroxide is 1 to 50 equivalent to the β-hydroxythiol ester For the treatment with hydrogen peroxide, it is preferable to previously cool the reaction mixture to −25° C. to room temperature.

The β-Aminothiol ester of the present invention having the general formula (I) is prepared according to the process of the present invention in a mixture of the 2(S),3(R)-form and 2(R),3(S)-form with respect to the configuration at the 2-position and the 3-position of pentanoic acid thioester, wherein the 2(S),3(R)-form is predominantly formed. As mentioned in the following Reference Example 10, a ratio of the 2(S),3(R)-form and 2(R),3(S)-form is in some case 9:1 in favor of the 2(S),3(R)-form, which can be suitably converted to carbapenem antibiotics. Though the mixture may be separated into each diastereoisomer after ring closure, they as such can also be subjected to separation by means of high performance liquid chromatography (HPLC).

The present invention is more particularly described and explained in the following Reference Examples and Examples. However, it is to be understood that the present invention is not limited to the Reference Examples and Examples and various changes and modifications may be made without departing from the spirit and scope of the present invention.

REFERENCE EXAMPLE 1

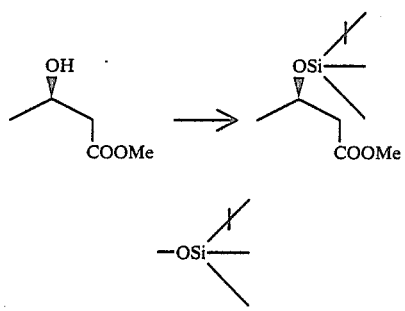

hereinafter refers to t-butyldimethylsilyloxy group.

There were dissolved 5.91 g (50 mmol) of methyl 3-hydroxybutyrate and 3.74 g (55 mmol) of imidazole in 20 ml of DMF, to which 8.29 g (55 mmol) of t-butyldimethylsilyl chloride was added by several portions. After stirring at room temperature for 30 minutes, ice-water was added to the reaction mixture and the resultant was extracted with diethyl ether for three times. Extract was washed with a saturated solution of salt and dried with anhydrous magnesium sulfate, followed by concentration under reduced pressure. The obtained concentrated liquid was distilled (at 62° to 68° C., 5 mmHg) to give 10.51 g of (—)-methyl 3-t-butyldimethylsilyloxybutyrate (yield: 91%).

Thin layer chromatography: Rf=0.4 (hexane:diethyl ether=20:1).

Infrared absorption spectrum (cm$^{-1}$): 1735 (neat).

Nuclear magnetic resonance spectrum δ: 0.03, 0.06 (each 3H; s), 0.85 (9H; s), 1.20 (3H; d J=5), 2.42 (2H; m), 3.75 (3H; s) and 4.25 (1H; m).

Mass spectrum (m/e): 115, 133, 159 (M-(Me+-COOMe)), 175 (M-Bu) and 217 (M-Me).

$[\alpha]_D^{20} = -31.75°$ (c=1.94, CHCl$_3$).

REFERENCE EXAMPLE 2

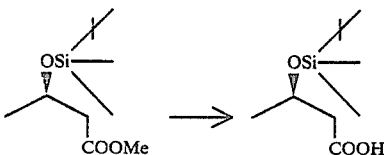

There was dissolved 3.58 g (15.4 mmol) of (—)-methyl 3-t-butyldimethylsilyloxybutyrate in 30 ml of methanol, to which 30 ml of 1N potassium hydroxide solution was added and the resultant mixture was stirred for 15 hours. After most of methanol was distilled away, the resultant was acidified with 1N hydrochloric acid and extracted with diethyl ether. Extract was washed with a saturated solution of salt and dried with anhydrous magnesium sulfate, followed by concentration under reduced pressure to give 3.18 g of 3-t-butyldimethylsilyloxy butyric acid (yield: 95%).

Thin layer chromatography: Rf=0.2 (hexane:diethyl ether=20:1).

Infrared absorption spectrum (cm$^{-1}$): 1710 (neat).

Nuclear magnetic resonance spectrum δ: 0.09 (6H; s), 0.88 (9H; s), 1.20 (3H; d J=6), 2.46 (2H; d J=6) and 4.27 (1H; dt J=6.6).

Mass spectrum (m/e): 110, 137, 197 and 218 (M).

$[\alpha]_D^{20} = -12.50°$ (c=0.96, chloroform).

REFERENCE EXAMPLE 3

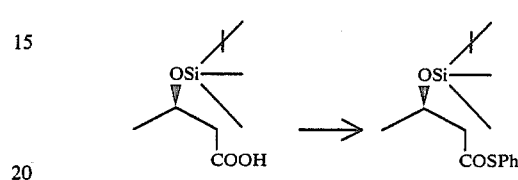

There were dissolved 3.18 g (19.2 mmol) of (—)-3-t-butyldimethylsilyloxybutyric acid and 2.26 ml (22 mmol) of thiophenol in 100 ml of methylene chloride, to which 4.53 g (22 mmol) of N,N'-dicyclohexylcarbodiimide was added. After stirring at room temperature for 2 hours, the resultant was filtered, filtrate being concentrated and distilled (at 110° to 116° C./0.3 mmHg) to give 5.00 g of (—)-S-phenyl-3-t-butyldimethylsilyloxybutanethioate (yield: 83%).

Thin layer chromatography: Rf=0.3 (hexane:diethyl ether=20:1).

Infrared absorption spectrum (cm$^{-1}$): 1710 (neat).

Nuclear magnetic resonance spectrum δ: 0.07 (6H; s), 0.91 (9H; s), 1.22 (3H; d J=5), 2.61, 2.87 (each 1H; dd J=15.7), 4.34 (1H; m) and 7.41 (5H; s).

Mass spectrum (m/e): 115, 159 (M-(Me+COSPh)), 253 (M-Bu) and 295 (M-Me).

$[\alpha]_D^{20} = -65.91°$ (c=0.98, CHCl$_3$).

REFERENCE EXAMPLE 4

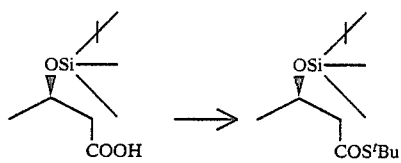

There were dissolved 218 mg (1 mmol) of (—)-3-t-butyldimethylsilyloxybutryic acid and 0.11 ml (1 mmol) of t-butyl mercaptan in 5 ml of methylene chloride, to which 206 mg (1 mmol) of N,N'-dicyclohexylcarbodiimide and 5 mg of N-dimethylaminopyridine were added and the resultant was stirred at room temperature for 3 days. The reaction solution was chromatographed on 10 g of silica-gel (C-200, developing solvent; methylene chloride) to give 231 mg of (—)-S-t-butyl-3-t-butyldimethylsilyloxybutanethioate (yield: 80%).

Thin layer chromatography: Rf=0.5 (hexane:diethyl ether=20:1).

Infrared absorption spectrum (cm$^{-1}$): 1685 (neat).

Nuclear magnetic resonance specrum δ: 0.04 (6H; s), 0.84 (9H; s), 1.16 (3H; d J=6), 1.41 (9H; s), 2.38, 2.66 (each 1H; dd J=15.7) and 4.26 (1H; m).

Mass spectrum (m/e): 119, 135, 159, 177, 233 (M-Bu) and 275 (M-Me).

$[\alpha]_D^{20} = -47.65°$ (c=0.94, CHCl$_3$).

REFERENCE EXAMPLE 5

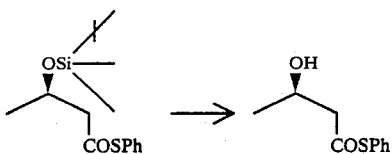

To 3.26 g (10.4 mmol) of (—)-S-phenyl-3-t-butyl-dimethylsilyloxybutanethioate was added 50 ml of mixture of acetic acid, THF and water (3:1:1), which was stirred at 50° C. for 24 hours. The resultant was concentrated and distilled (at 128° to 130° C./0.8 mmHg) to give 1.91 g of (—)-S-phenyl-3-hydroxybutanethioate (yield: 94%).

Thin layer chromatography: Rf=0.35 (hexane-diethyl ether=1:1).

Infrared absorption spectrum (cm$^{-1}$): 3440 and 1705 (neat).

Nuclear magnetic resonance spectrum δ: 1.20 (3H; d J=6), 2.82 (2H; d J=6), 3.0 (1H; br. s), 4.22 (1H; m) and 7.36 (5H; s).

Mass spectrum (m/e): 110 (PhSH), 137 (COSPh) and 196 (M).

$[\alpha]_D^{20}=-42.25°$ (c=1.42, CHCl$_3$).

REFERENCE EXAMPLE 6

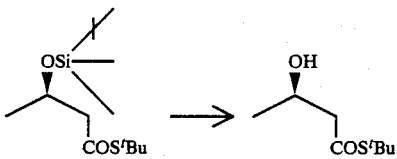

There was dissolved 1.55 g (5.33 mmol) of (—)-S-t-butyl-3-t-butyldimethylsilyloxybutanethioate in 25 ml of a mixture of acetic acid, THF and water (3:1:1) and the resultant was stirred at 50° to 55° C. for 2 days. The reaction solution was concentrated under reduced pressure and purified with silica-gel column chromatography (40 g of silica-gel, developing solvent; hexane:diethyl ether=2:1) to give 755 mg (4.28 mmol) of (—)-S-t-butyl-3-hydroxybutanethioate (yield: 80%).

Thin layer chromatography: Rf=0.45 (hexane:diethyl ether=1:1).

Infrared absorption spectrum (cm$^{-1}$): 3430 and 1680 (neat).

Nuclear magnetic resonance spectrum δ: 1.19 (3H; d J=6), 1.44 (9H; s), 2.57 (2H, d J=5), 3.4 (1H; br. s) and 4.18 (1H; m).

Mass spectrum (m/e): 98, 120, 143, 148 and 177 (M+1).

$[\alpha]_D^{20}=-41.83°$ (c=1.96, chloroform).

EXAMPLE 1

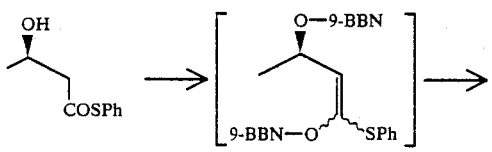

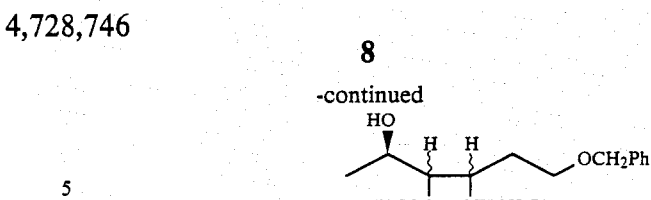

There were added 820 mg (5.0 mmol) of 3-benzyloxy-propionaldehyde, 0.55 ml (5.0 mmol) of benzylamine and 1 g of magnesium sulfate to 10 ml of diethyl ether and the resultant was stirred for 30 minutes. The reaction solution was filtered and washed with benzene, filtrate being concentrated. The obtained imine was used in the following reaction without further purification.

There was dissolved 806 mg (4.11 mmol) of (—)-S-phenyl-3-hydroxybutanethioate in 16 ml of methylene chloride, to which 1.50 ml (8.6 mmol) of diisopropylamine, 2.27 g (8.4 mmol) of 9-borabicyclo-[3.3.1]nonyl trifluoromethanesulfonate (hereinafter referred to as "9-BBN triflate") were added at —70° C. After stirring at —70° C. for 30 minutes, a temperature of the mixture was raised to —35° C. for 15 minutes and stirring was further continued at —35° C. to —20° C. for 1 hour, to which a solution of the previously prepared imine in 20 ml of methylene chloride was added. A temperature of the mixture was raised to —20° C. to 5° C. for 1.5 hour and stirring was further continued at room temperature for 1.5 hour. To the resultant were added under cooling with ice-water 20 ml of phosphate buffer (pH 7.0), 20 ml of methanol and 10 ml of 35% hydrogen peroxide solution and the mixture was stirred at 0° C. for 15 minutes and then at room temperature for 10 minutes, followed by extraction with methylene chloride for two times. Extract was washed with a saturated solution of salt, dried with anhydrous sodium sulfate and concentrated under reduced pressure, which was purified with silica-gel column chromatography for two times (70 g of silica-gel, C-300, developing solvent; hexane:diethyl ether=3:2, and then 100 g of silica-gel, developing solvent; hexane:diethyl ether=2:1 to 1:2) to give 304 mg of starting (—)-S-phenyl-3-hydroxybutanethioate and 672 mg of 3-benzylamino-5-benzyloxy-2-(1-hydroxyethyl)pentanoic acid phenylthio ester (yield: 36%, yield based on consumed starting material: 58%).

Thin layer chromatography: Rf=0.28 (hexane:diethyl ether=1:1).

Infrared absorption spectrum (cm$^{-1}$): 3350 and 1705 (neat).

Nuclear magnetic resonance spectrum δ: 1.24 (3H; d J=6), 2.0 (2H; m), 2.98 (1H; dd J=3.6), 3.1 to 3.7 (5H; m), 3.68, 3.87 (each 1H; d J=13), 4.4 (1H; m), 4.38 (2H; s), 7.20, 7.23 (10H; each s) and 7.33 (5H; s).

Mass spectrum (m/e): 145, 160, 189, 200, 254, 311, 340 (M-SPh) and 358 (M-PhCH$_2$).

EXAMPLE 2

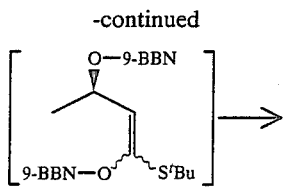

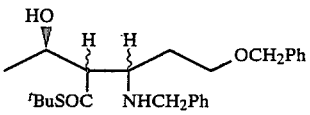

There were added 1.642 g (10.0 mmol) of 3-benzyloxypropionaldehyde, 1.09 ml (10.0 mmol) of benzylamine and 2 g of magnesium sulfate to 20 ml of diethyl ether and the resultant was stirred for 30 minutes. The reaction solution was filtered and washed with benzene, filtrate being concentrated. The obtained imine was used in the following reaction without further purification.

There was dissolved 1.492 g (8.46 mmol) of (−)-t-butyl-3-hydroxybutanethioate in 40 ml of methylene chloride, to which 3.13 ml (18 mmol) of diisopropylamine, 4.59 g (17 mmol) of 9-BBN triflate were added at −70° C. After stirring at −25° C. to −10° C. for 1 hour, a solution of the previously prepared imine in 40 ml of methylene chloride was added to the mixture, which was further stirred at −10° C. to 15° C. for 4 hours. To the resultant were added under cooling with ice-water 60 ml of phosphate buffer (pH 7.0), 60 ml of methanol and 30 ml of 31% hydrogen peroxide solution and the mixture was stirred under cooling with ice for 15 minutes and then at room temperature for 40 minutes, followed by extraction with methylene chloride for two times. Extract was washed with a saturated solution of salt, dried with anhydrous sodium sulfate and then concentrated, which was separated with silica-gel column chromatography (150 g of silica-gel, C-300, developing solvent; diethyl ether:hexane=2:1) to give 838 mg of 3-benzylamino-5-benzyloxy-2-(1-hydroxyethyl)pentanoic acid t-butylthio ester, which contained impurities, mainly benzyl alcohol.

Thin layer chromatography: Rf=0.34 (hexane-diethyl ether=1:1).

Infrared absorption spectrum (cm$^{-1}$): 3400 and 1680 (neat).

Nuclear magnetic resonance spectrum δ: 1.25 (3h; d J=6), 1.43 (9H; s), 2.0 (2H, m), 2.78 (1H; dd J=3.8), 3.1 to 3.9 (7H; m), 4.28 (1H; m), 4.42 (2H; s), 7.21 (5H; s) and 7.23 (5H; s).

Mass spectrum (m/e): 254, 294, 328, 338 (M-PhCH$_2$), 372 (M-Bu) and 430 (M+1).

REFERENCE EXAMPLE 7

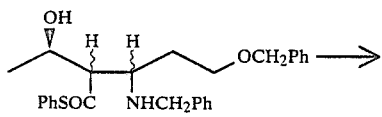

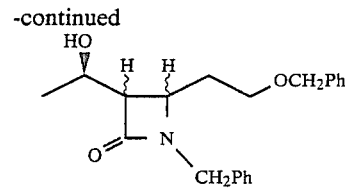

There was dissolved 752 mg (1.67 mmol) of 3-benzylamino-5-benzyloxy-2-(1-hydroxyethyl)pentanoic acid phenylthio ester in 10 ml of THF, to which 448 mg (4.0 mmol) of potassium t-butoxide, a suspension of 0.2 ml of water and 5 ml of THF, and 0.6 ml of water were added. After stirring at room temperature for 6 hours, the reaction mixture was neutralyzed with 1N hydrochloric acid, subjected to salting-out and extracted with ethyl acetate for six times. An organic layer was concentrated and concentrated liquid was added to 150 ml of acetonitrile, to which 440 mg (2.0 mmol) of 2,2-dipyridyl disulfide was added, to which a solution of 525 mg (2.0 mmol) of triphenylphosphine in 30 ml of acetonitrile was added dropwise for 20 minutes and the resultant was heated under reflux for 3 hours. After concentrating the reaction solution, a fraction of the desired compound also containing 2-pyridothion was obtained with silica-gel chromatography (60 g of silica-gel, developing solvent; diethyl ether), the fraction being washed with 1N sodium hydroxide, water and a saturated solution of salt, dried with anhydrous sodium sulfate and concentrated to give 410 mg of 1-benzyl-4-(2-benzyloxyethyl)-3-(1-hydroxyethyl)-2-azetizinone (yield: 72%).

Thin layer chromatography: Rf=0.25 (diethyl ether).

Infrared absorption spectrum (cm$^{-1}$): 3460 and 1735 (chloroform).

Nuclear magnetic resonance spectrum δ: 1.23 (3H; d J=6), 1.8 (3H; m), 2.87 (8/9H; dd J=6.3), 3.14 (1/9H; m), 3.3 to 3.7 (3H; m), 3.8 to 4.2 (2H; m), 4.32, 4.35 (2H; each s), 4.56 (1H; d J=15), 7.23 and 7.26 (10H; each s).

Mass spectrum (m/e): 91, 146, 160, 199, 201, 277 and 311.

REFERENCE EXAMPLE 8

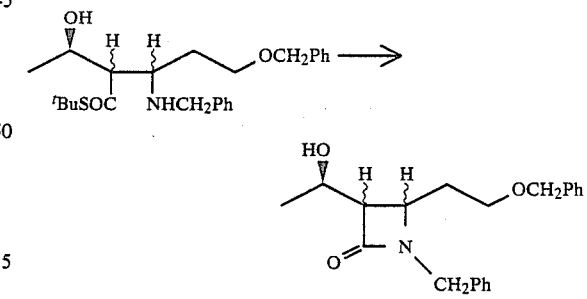

There was dissolved 838 mg of 3-benzylamino-5-benzyloxy-2-(1-hydroxyethyl)pentanoic acid t-butylthio ester, which contained impurities, mainly benzyl alcohol, in 20 ml of THF, to which 1 ml of 4N potassium hydroxide solution was added. After stirring at 45° C. for two days, the reaction mixture was neutralyzed with 1N hydrochloric acid, subjected to salting-out and extracted with ethyl acetate for six times. An organic layer was concentrated and concentrated liquid was dissolved in 150 ml of acetonitrile, to which 440 mg (2.0 mmol) of 2,2-dipyridyl disulfide and 525 mg (2.0 mmol)

of triphenylphosphine were added and the resultant was heated under reflux for 6 hours. After concentrating the reaction solution, a fraction of the desired compound also containing 2-pyridothion was obtained with silica-gel chromatography (60 g of silica-gel, developing solvent: diethyl ether), the fraction being washed with 1N sodium hydroxide, water and a saturated solution of salt, dried with anhydrous sodium sulfate and concentrated to give 51 mg of 1-benzyl-4-(2-benzyloxyethyl)-3-(1-hydroxyethyl)-2-azetizinone, spectrum data of which were completely agreed with those obtained in Reference Example 7.

REFERENCE EXAMPLE 9

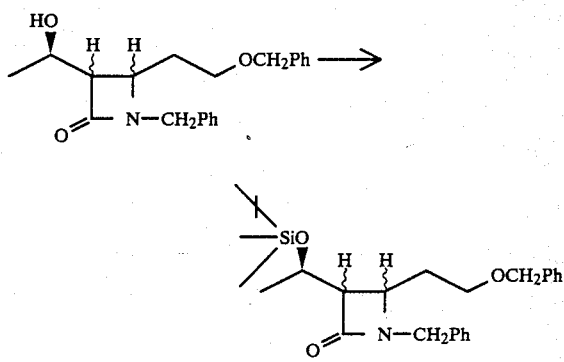

There was dissolved 100 mg (0.3 mmol) of 1-benzyl-4-(2-benzyloxyethyl)-3-(1-hydroxyethyl)-2-azetizinone in 5 ml of methylene chloride, to which 0.06 ml (0.5 mmol) of 2,6-lutidine and 0.09 ml (0.04 mmol) of t-butyldimethylsilyl triflate were added under cooling with ice-water. After stirring at room temperature for 5 minutes, the resultant was cooled with ice-water and extracted with methylene chloride for two times. Extract was added with sodium bisulate and lutidine was removed, followed by concentration and purification with silica-gel column chromatography (C-300; 10 g of silica-gel, developing solvent; hexane:diethyl ether=1:1) to give 128 mg of 1-benzyl-4-(2-benzyloxyethyl)-3-(1-t-butyldimethylsilyloxyethyl)-2-azetizinone (yield: 89%).

Thin layer chromatography: Rf=0.45 (hexane:-diethyl ether=1:1).

Infrared absorption spectrum (cm$^{-1}$): 1740 (chloroform).

Nuclear magnetic resonance spectrum δ: 0.04, 0.08 (each 3H, s), 0.84 (9H; s), 1.14 (3H; d J=6), 1.8 (2H; m), 2.82 (8/9H; dd J=2.6), 3.15 (1/9H; m), 3.35 (2H; m), 3.67 (1H; m), 4.0 to 4.6 (3H; m), 4.43 (2H; s), 7.24 and 7.27 (10H: each s).

Mass spectrum (m/e): 91, 290, 396 (M-Bu) and 438 (M-Me).

REFERENCE EXAMPLE 10

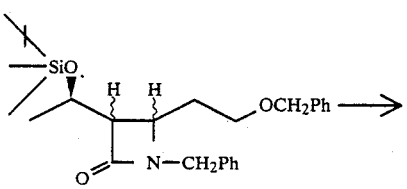

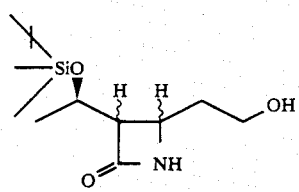

To 120 mg of sodium was added about 5 ml of liquid ammonia at −70° C. An obtained blue solution was added with a solution of 99 mg (0.28 mmol) of 3-(1-t-butyldimethylsilyloxyethyl)-4-(2-hydroxyethyl)-2-azetizinone in 2 ml of diethyl ether and stirred at −70° C. to −50° C. for 1 hour, to which saturated solution of ammonium chloride was added and left to stand to 0° C. The resultant was extracted with dichloromethane, extract being washed with a saturated solution of salt, dried with anhydrous magnesium sulfate and concentrated under reduced pressure, followed by purification with silica-gel column chromatography (10 g of silica-gel; C-300, developing solvent; diethyl ether to diethyl ether:methanol=20:1) to give 59 mg of 3-(1-t-butyl-dimethylsilyloxyethyl)-4-(2-hydroxyethyl)-2-azetizinone (yield: 76%).

Thin layer chromatography: Rf=0.17 (diethyl ether).

Infrared absorption spectrum (cm$^{-1}$): 3440 and 1750 (chloroform).

Nuclear magnetic resonance spectrum δ: 0.12 (6H; s), 0.92 (9H; s), 1.27 (3H; d J=6), 1.88 (2H; m), 2.55 (1H; br. s), 2.91 (1H; m), 3.74 (3H; m), 4.17 (1H; m) and 6.4 (1H; br. s).

Mass spectrum (m/e): 75, 216 (M-Bu) and 258 (M-Me).

By employing 2,2-dimethyoxypropane and BF$_3$.O-Et$_2$, 3-(1-t-butyldimethylsilyloxyethyl)-4-(2-hydroxyethyl)-2-azetizinone was converted to 7-(1-t-butyldimethylsilyloxyethyl)-2,2-dimethyl-3-oxa-1-azabicyclo[4.2.-0]octan-8-one, which was then treated with tetrabutylammonium fluoride to give 7-(1-hydroxyethyl)-2,2-dimethyl-3-oxa-1-azabicyclo[4.2.0]octan-8-one, which is known in the literature (F. A. Bouffard, D. B. R. Johnston, and B. G. Christensin, J. Org. Chem., 45, 1130 (1980)). Composition of nuclear magnetic resonance spectrum showed that obtained 7-(1-hydroxyethyl)-2,2-dimethyl-3-oxa-1-azabicyclo[4.2.0]octan-8-one was a mixture of two kinds of stereoisomer (about 9:1). Main product was 6(R),7(S)-(1(R)-hydroxyethyl)-2,2-dimethyl-3-oxa-1-azabicyclo[4.2.0]octan-8-one, which can be converted to carbapenem antibiotics such as thienamycin, and by-product was 6(R),7(R)-(1(R)-hydroxyethyl)-2,2-dimethyl-3-oxa-1-azabicyclo[4.2.-0]octan-8-one.

REFERENCE EXAMPLE 11

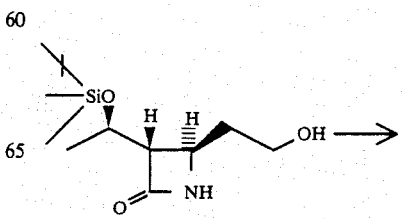

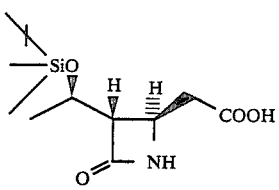

A mixture of diastereoisomer obtained in Reference Example 10 was separated with silica-gel column chromatography and 95 mg (0.35 mmol) of the thus obtained 3(S)-[1(R)-t-butyldimethylsilyloxyethyl]-4(R)-(2-hydroxyethyl)-2-azetizinone was dissolved in 1.5 ml of pyridine, which was added under cooling with ice to Sarett reagent prepared from 150 mg of chromic acid and 1.5 ml of pyridine. After stirring at room temperature for one night, inorganic salt was removed with silica-gel column chromatography (10 g of silica-gel, developing solvent; ethyl acetate) and pyridine was removed by azetrope with toluene, followed by purification with silica-gel column chromatography (5 g of silica-gel, developing solvent; diethyl ether) to give 76 mg of 3(S)-[1(R)-t-butyldimethylsilyloxyethyl]-4(R)-carboxymethyl-2-azetizinone (yield: 76%). Samples for analysis were obtained by recrystallization from diethyl ether.

Thin layer chromatography: Rf=0.2 (diethyl ether).
Melting point: 151° to 154° C. (decomposition).
Infrared absorption spectrum (cm$^{-1}$): 3310, 1750 and 1730 (chloroform).
Nuclear magnetic resonance spectrum δ: 0.08 (6H; s), 0.82 (9H; s), 1.21 (3H; d J=7), 2.3 to 3.0 (3H; m), 3.9 (1H; m), 4.16 (2H; m), 7.0 (1H; br. s) and 8.1 (1H; br. s).
Mass spectrum (m/e): 186, 230 (M-Bu) and 272 (M-Me).
Elementary analysis: for $C_{13}H_{25}O_4NSi$: Calcd. (%): C 54.32 H 8.77 N 4.87. Found (%): C 54.07 H 8.72 N 4.80.
$[\alpha]_D^{20} = +16.19°$ (c=1.00, chloroform).

REFERENCE EXAMPLE 12

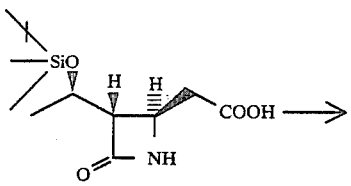

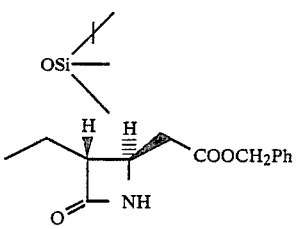

There were dissolved 56 mg (0.20 mmol) of 4(R)-carboxymethyl-3(S)-[1(R)-t-butyldimethylsilyloxyethyl]-2-azetizinone and 27 mg (0.25 mmol) of benzyl alcohol in 3 ml of methylene chloride, to which 52 mg (0.25 mmol) of N,N'-dicyclohexylcarbodiimide and a spoonful of N,N-dimethylaminopyridine were added and the mixture was stirred at room temperature for 2 hours. The reaction solution was concentrated and purified with silica-gel column chromatography (10 g of silica-gel, C-300, developing solvent; hexane:diethyl ether=1:2) to give 59 mg of 4(R)-benzyloxymethyl-3(S)-[1(R)-t-butyldimethylsilyloxyethyl]-2-azetizinone (yield: 80%). Samples for analysis were obtained by recrystallization from diethyl ether and hexane.

Thin layer chromatography: Rf=0.26 (diethyl ether:hexane=2:1).
Melting point: 93.5 to 94.5° C.
Infrared absorption spectrum (cm$^{-1}$): 3450, 1765 and 1735 (chloroform).
Nuclear magnetic resonance spectrum δ: 0.07 (6H; s), 0.88 (9H; s), 1.21 (3H; d J=7), 2.5 to 2.9 (3H; m), 4.0 (1H; m), 4.2 (2H; m), 5.18 (2H; s), 5.95 (1H; br. s) and 7.37 (5H; s).
Mass spectrum (m/e): 232, 276 and 320 (M-Bu).
Elementary analysis: $C_{20}H_{31}O_4NSi$: Calcd. (%): C 63.63 H 8.28 N 3.71. Found (%): C 63.61 H 8.24 N 3.71.
$[\alpha]_D^{20} = +16.59°$ (c=1.00, chloroform).

REFERENCE EXAMPLE 13

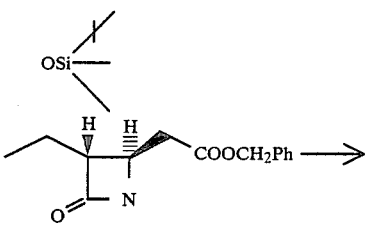

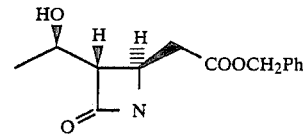

There was added 2 ml of a mixture of acetic acid, THF and water (3:1:1) to 57 mg (0.15 mmol) of 4(R)-benzyloxymethyl-3(S)-[1(R)-t-butyldimethylsilyloxyethyl]-2-azetizinone and stirred at 50° to 60° C. for 30 hours. The reaction solution was concentrated at lowered temperature and under reduced pressure and purified with silica-gel chromatography (5 g of silica-gel, C-200, developing solvent; ethyl acetate) to give 35 mg of 4(R)-benzyloxymethyl-3(S)-[1(R)-hydroxyethyl]-2-azetizinone (yield: 89%).

$[\alpha]_D^{20} = +9.84°$ (c=2.1, chloroform)

Spectrum data of the product were completely agreed with those described in the literature (D. G. Melillo, T. Liu, K. Ryan, M. Sletzinger and I. Shinkai, Tetrahydron Letter, 22, 913 (1981)) except the optical rotation. The literature shows that the above product is converted to thienamycin. The value of the optical rotation of the product nearly agreed with that described in the literature (N. Ikota, O. Yoshino and K. Koga, Chem. Pharm. Bull., 30, 1929 (1982)), $[\alpha]_D^{20} = +9.9°$ (c=2.3, chloroform).

What we claim is:
1. A β-Aminothio ester having the formula (I):

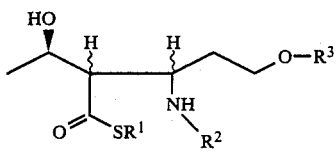
(I)

wherein $R^1$ is an alkyl group having from 1 to 4 carbon atoms or phenyl, $R^2$ is an amino-protecting group selected from the group consisting of benzyl, methoxyphenyl, and trialkylsilyl wherein each alkyl group has from 1 to 4 carbon atoms, and $R^3$ is a hydroxy-protecting group selected from the group consisting of benzyl, tetrahydropyranyl, and trialkylsilyl wherein each alkyl group has from 1 to 4 carbon atoms.

2. A process for preparing a β-hydroxythiol ester having the formula (I):

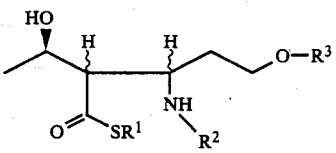
(I)

wherein $R^1$ is an alkyl group having from 1 to 4 carbon atoms or phenyl, $R^2$ is an amino-protecting group selected from the group consisting of benzyl, methoxyphenyl, and trialkylsilyl wherein each alkyl group has from 1 to 4 carbon atoms, and $R^3$ is a hydroxy-protecting group selected from the group consisting of benzyl, tetrahydropyranyl, and trialkylsilyl wherein each alkyl group has from 1 to 4 carbon atoms, which comprises reacting a β-hydroxythiol ester having the formula (III):

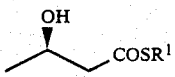
(III)

where $R^1$ is as above, with a boron compound having the formula (IV):

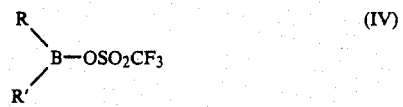
(IV)

wherein each of R and R' is an alkyl group or a cycloalkyl group, or R and R' taken together form a ring including the boron atom, in the presence of a tertiary amine, the obtained reaction mixture being reacted with an imine having the formula (V):

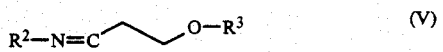
(V)

wherein $R^2$ and $R^3$ are as above, followed by treating the resultant product with hydrogen peroxide.

3. A β-Hydroxythiol ester having the formula (III):

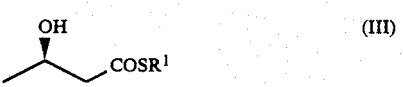
(III)

wherein $R^1$ is an alkyl group having from 1 to 4 carbon atoms or phenyl.

* * * * *